(12) United States Patent
Jayaraman et al.

(10) Patent No.: US 9,473,493 B2
(45) Date of Patent: Oct. 18, 2016

(54) SECURE DATA COMMUNICATION (71) Applicant: Tata Consultancy Services Limited, Mumbai (IN)

(72) Inventors: Srinivasan Jayaraman, Bangalore (IN); Balamuralidhar Purushothaman, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 583 days.

(21) Appl. No.: 14/041,301

(22) Filed: Sep. 30, 2013

(65) Prior Publication Data

US 2016/0219047 A1 Jul. 28, 2016

(30) Foreign Application Priority Data

Oct. 22, 2012 (IN) .......................... 3086/MUM/2012

(51) Int. Cl.
*H04L 29/06* (2006.01)
(52) U.S. Cl.
CPC ....... *H04L 63/0861* (2013.01); *H04L 63/0428* (2013.01)
(58) Field of Classification Search
CPC ...................... H04L 63/0861; H04L 63/0428
USPC ............................................................ 726/7
See application file for complete search history.

(56) References Cited

U.S. PATENT DOCUMENTS 8,135,957 B2    3/2012  Dinges et al.
2010/0088749 A1*  4/2010  Steeples .............. H04L 63/0853
                                                                726/4

OTHER PUBLICATIONS

K.V.R, Ravi et al: "Data Encryption Using Event-related Brain Signals", International Conference on Computational Intelligence and Multimedia Applications, Dec. 1, 2007, pp. 540-544.*
Ramaswamy Pafaniappan et al: "PIN Generation Using Single Channel EEG Biometric", Networked Digital Technologies, 1. January 2G 1.1 (Jan. 1, 2011), Springer Berlin Heidelberg, Berlin, Heidelberg.*
"European Application Serial No. EP13186663, European Search Report mailed Feb. 4, 2014", 11 pgs.
Liwen, Fei Su, et al., "A Dual-Biometric-Modality Identification System Based on Fingerprint and EEG", *2010 Fourth IEEE International Conference on Biometrics: Theory Applications and Systems (BTAS)*, (2010), 6 pgs.
Martens, S.M.M., et al., "A Graphical Model Framework for Decoding in the Visual ERP-Based BCI Speller", *Neural Computation* 23, (2011), (2010), 160-182.

(Continued)

*Primary Examiner* — Longbit Chai
(74) *Attorney, Agent, or Firm* — Schwegman Lundberg & Woessner, P.A.

(57) ABSTRACT

A system and a method for secure data communication over a network are described. In one embodiment, a method comprises generating a visual flashing code containing encrypted data, wherein the visual flashing code is transmitted to a user on a user device. Further, the method comprises obtaining real time biometric data of the user from at least one biometric device connected to the user device. Furthermore, the method comprises authenticating the user based on the real time biometric data. Upon authentication, the encrypted data is decrypted at the user device based on electroencephalogram (EEG) data obtained from an EEG device, wherein the EEG data comprises brain signals indicative of brain activity of the user corresponding to the visual flashing code.

20 Claims, 5 Drawing Sheets

(56) References Cited

OTHER PUBLICATIONS

Palaniappan, Ramaswamy, et al., "PIN Generation Using Single Channel EEG Biometric", *In: Networked Digital Technologies*, A. Abraham, et al. (Editors), Springer-Verlag Berlin Heidelberg, Berlin, Germany, (2011), 378-385.

Rathgeb, Christian, et al., "A survey on biometric cryptosystems and cancelable biometrics", *EURASIP Journal on Information Security*, vol. 2011, No. 1, (2011), 25 pgs.

Ravi, K. V. R., et al., "Data encryption using event-related brain signals", *International Conference on Computational Intelligence and Multimedia Applications (ICCIMA 2007)*, (2007), 540-544.

\* cited by examiner

SECURE DATA COMMUNICATION

TECHNICAL FIELD

The present subject matter relates, in general to, data security and, in particular to, a system and a method for secure data communication over a network.

BACKGROUND

With the advancement in technology, several methods of data communication over a network, such as the Internet, have come into existence. To make the data communication between two parties, i.e., a sender and a receiver secure, it needs to be ensured that access to the data being communicated is limited to the two parties only. In other words, the privacy of the sender and receiver needs to be maintained. The importance of privacy is even more when communication involves transmission of data that is sensitive to either or both the parties. Data sent over communication channels, such as a physical wire, radio, and laser is susceptible to be tapped and misused.

Several measures have been developed to ensure secure communication of data. The requirement of any data communication system is that the data is sent to or received by only the intended recipient. The requirement for secure communication may be achieved by means of an authentication system which allows access of data only after authenticating the recipient. Further, when data is transmitted over Internet other security risks also exist. For example, the data being intercepted by a third party also poses threat to secure communication.

Conventionally, encryption techniques are employed to overcome such risks. Encryption of data involves encoding the data, using a code, at the sender's end. A corresponding code is made available to the intended recipients in order to decrypt the data at the receiver's end. This ensures that the data can be accessed only by the intended parties and not by any third party. Though several encryption techniques are conventionally known, the conventional techniques are often subject to various shortcomings. For example, some conventional techniques may be very complicated and consume a lot or resources in their implementation. Also, some existing techniques may be susceptible to attack by fraudulent entities.

SUMMARY

This summary is provided to introduce concepts related to a secure data communication over the network and these concepts are further described below in the detailed description. This summary is not intended to identify essential features of the claimed subject matter nor is it intended for use in determining or limiting the scope of the claimed subject matter.

In one embodiment, a method for secure data communication over a network comprises generating a visual flashing code containing encrypted data, wherein the visual flashing code is transmitted to a user on a user device. Further, the method comprises obtaining real time biometric data of the user from at least one biometric device connected to the user device. Furthermore, the method comprises authenticating the user based on the real time biometric data. Upon authentication, the encrypted data is decrypted at the user device based on electroencephalogram (EEG) data obtained from an EEG device, wherein the EEG data comprises brain signals indicative of brain activity of the user corresponding to the visual flashing code.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the figures to reference like features and components.

DETAILED DESCRIPTION

Secure data communication over a network, such as an Internet, is one of the most important issues in many businesses and industries. With the advent of technology, large volume of data is transmitted over the networks. Some data can be of sensitive nature, for example, private data of a user. Transmission of such data needs to be made secure such that misuse of the sensitive data is avoided. Conventional methods of the secure data communication over a network involve authentication, and/or encryption/decryption of the data.

The authentication process is used to validate identity of a user in order to ensure that the data is being accessed by the intended user. In certain scenarios, it is of crucial importance that only authorized person access the data. For example, in research facilities and government institutions only authorized person have access to the data, as the data involved therein is very sensitive and should not get into the hands of an unintended user. Therefore, a system to authenticate the user is required. A usual method of authentication is achieved by means of login credentials.

Further, in order to ensure that sensitive data, which may include personal information, and password pertaining to the user, is accessed only by the intended user and not intercepted by a fraudulent third party while transmission through the network, an encryption system is employed. Typical encryption systems based on public-private key has weaknesses, such as the public key is susceptible to brute force attack or the private key could be accidently exposed to a third party.

In certain cases, a combination of both key-based encryption and login-based authentication are employed. For example, the data is encrypted using the key-based encryption techniques at a data server and access to the data server is restricted using passwords and/or certificates. However, such a conventional system fails to protect the communication path during the transmission. For example, once the encrypted data was sent out from a sender, the encrypted data may be hacked or altered before reaching the recipient, and after a user is allowed access to the data exchange server and starts downloading or uploading data, the data may be intercepted, eavesdropped, or filtered to hack the information contained therein.

One example of application of secure data communication is in electronic transactions, such as on-line shopping and on-line banking, where a user is initially authenticated and authorized using the username and password to log on to a secured site. During such electronic transactions, a disguised user may log on to access the secured site, or the user may be led to an unintended site which tries to obtain personal information from the user. However, the conventional security system that are employed in a banking industry or e-commerce industry are not reliable in confirming that the identity of the user is still the same authenticated user, and that the server is still the same server. One way of confirming identity of the user which is employed by the banking industry, in the past few years, is transmitting a one time password (OTP) to the user on an external device, such as a mobile phone of the user that is registered with the online banking system. In such cases where authentication is based on the external devices, the security of the external device is also an issue, for example, the disguised user can make the net transaction, if that user has access to that external device of the authorized user.

In accordance with the present subject matter, a system and a method for secure data communication over the network in order to protect against data theft, or manipulation has been described. The method, according to one embodiment, includes encrypting the sensitive data to generate a visual flashing code at sender's end, transmitting the visual flashing code to the receiver, and decrypting the sensitive data at receiver's end, to ensure secure exchange of data between the sender such as a server, and the receiver such as a user. The system and the method can be implemented in a variety of communication devices, such as mobile phones, smart phones, personal digital assistants (PDAs), laptops, desktops, and the like. Although the description herein is with reference to certain devices, the system and method may be implemented in other devices, albeit with a few variations, as will be understood by a person skilled in the art.

In one implementation, sensitive data is encrypted at the server end, and transmitted in the form of a visual flashing code to a user device, such as mobile phone, PDA's, and computer, which may have requested the server for the sensitive data. The sensitive data may include any confidential data, including but not limited to, passwords and other business transaction related details. Although, the description herein is explained with respect to sensitive data, it will be appreciated by a person skilled in the art that any data other than the sensitive data can be encrypted and transmitted to the user device.

A visual flashing code may be understood as a visual stimulus flickering/flashing at different frequency levels. Such a visual flashing code can be generated in a predefined pattern, for example, a checkerboard pattern, black and white stripes pattern and an alpha-numeric keyboard pattern in a single color or a combination of different colors. The checkerboard pattern may be of a single or more than single checkerboard of same size or of different size. The back and white stripes pattern include a plurality of alternate black and white stripes. The alpha-numeric keyboard pattern generated may flicker at corresponding character or key for a predefined time interval. In one implementation, the visual flashing code is generated using any conventionally known visual flashing code generation method. The generation of visual flashing code may depend on various factors like the time of request/access, interval of request/access, and so on. The visual flashing code can be multi mode modulated in which a stimuli can contain one or more frequency in addition to the encrypted sensitive data. The transmitted visual flashing code can be displayed to the user on the user device.

In one implementation, an electroencephalogram (EEG) device for capturing the brain activity of a user, and one or more biometric devices for capturing physical and/or behavioral traits of a user, are employed at the user end for accomplishing secure data communication. In one implementation, the biometric devices, such as a fingerprint device, an Electrocardiogram (ECG) device, and/or a retina scanning device, can be used to obtain physical and/or behavioral traits, such as finger prints, heartbeats, and/or eye structures of the user based on which the user is authenticated, and the EEG device is used for capturing brain activity of the user, corresponding to the visual flashing code, viewing the visual flashing code based on which the sensitive data contained in the visual flashing code is decrypted. In one implementation, the decryption is carried out when the user is authenticated. The manner in which the authentication and decryption takes place is described henceforth.

A real time biometric data containing physical and/or behavioural traits of the user measured by the biometric device(s) is received from the user device, and transmitted to the server for authentication of the user. At the server, the authentication is performed based on comparing the real time biometric data with pre-stored biometric data of the user. Based on the comparison, the server may determine the user to be an authentic user who may be allowed to decrypt the encrypted sensitive data contained in the visual flashing code.

The decryption, as indicated herein, is performed based on EEG data containing signals indicative of the measured brain activity of the user, as obtained from the EEG device. The EEG data is processed at the user device and interpreted using a look-up table pre-stored within the local memory of the user device to decrypt the sensitive data. In one implementation, processing of the EEG data may include feature extraction, which can be performed using a conventionally known feature extraction technique.

Subsequent to decryption, the sensitive data can be displayed on the user device. In applications, such as online banking, e-commerce sites, where the sensitive data may be passwords or debit/credit card details, the decrypted sensitive data is not displayed to the user, rather the user can be automatically logged in subsequent to the decryption, thereby allowing the user to carry out the transactions.

The system and the method, thus, utilize a combination of the EEG and the biometrics for providing secure data communication between the server and the user over the network. According to the present subject matter, even if the sensitive data reaches the hands of an intruder or a hacker, the sensitive data would not be made accessible to user until identity of the user is validated based on biometric based authentication, and decryption is carried out based on the EEG. The system and the method, therefore, provide two layers of protection or security to the sensitive data being transmitted over the network. Additional layers of security, for example, login-credentials based authentication and other similar authentication of data security techniques known to a person skilled in the art can also be implemented.

The manner in which secure data communication is carried out is explained further in conjunction with FIGS. 1-4. While aspects of systems and methods may be implemented in any number of different computing systems, environments, and/or configurations, the embodiments are described in the context of the following exemplary system architecture(s).

Figure 1:
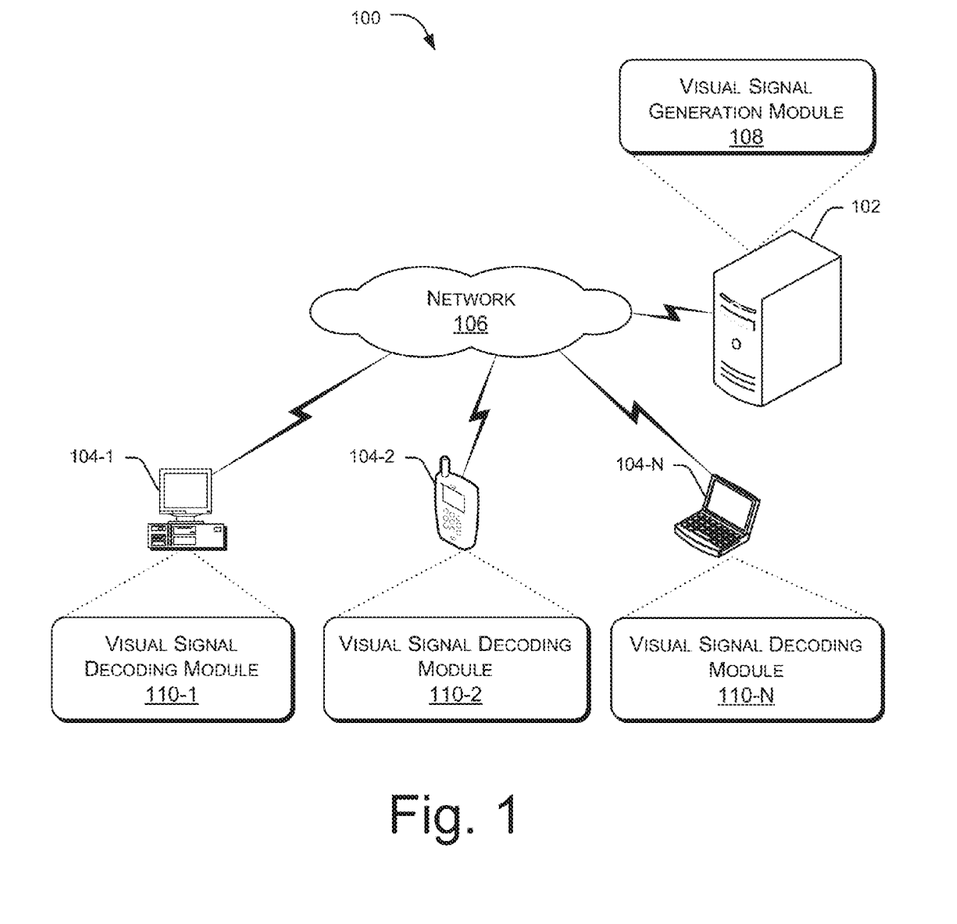
FIG. 1 illustrates a secure data communication system, in accordance with an embodiment of the present subject matter.

FIG. 1 illustrates a secure data communication system 100, in accordance with an embodiment of the present subject matter. The secure data communication system 100 (hereinafter referred to as a system 100) comprises a plurality of user devices 104-1, 104-2, . . . 104-N connected to an authentication server 102, through a network 106. The user devices 104-1, 104-2, . . . 104-N is collectively referred to as the user devices 104 and individually referred to as a user device 104. The user devices 104 and the authentication server 102 may be implemented as any of a variety of conventional computing devices, including, for example, servers, a desktop PC, a notebook or portable computer, a workstation, a mainframe computer, and an internet appliance. In one implementation, a plurality of users may use the user devices 104 to communicate with the authentication server 102.

The user devices 104 are connected to the authentication server 102 over the network 106 through one or more communication links. The communication links between the user devices 104 and the authentication server 102 are enabled through a desired form of communication, for example, via dial up, modem connections, cable links, digital subscriber lines (DSL), wireless or satellite links, or any other suitable form of communication.

The network 106 may be a wireless network, a wired network, or a combination thereof. The network 106 can also be an individual network or a collection of many such individual networks, interconnected with each other and functioning as a single large network, e.g., the Internet or Intranet. The network 106 can be implemented as one of the different types of networks, such as intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), etc., to communicate with each other. Further, the network 106 may include network devices, such as network switches, hubs, routers, Host Bus Adapters (HBAs), for providing a link between the user devices 104 and the authentication server 102. The network devices within the network 106 may interact with the user devices 104 and the authentication server 102 through the communication links.

In one implementation, the authentication server 102 (interchangeably referred to as server) may be a central authentication server of a banking industry transmitting sensitive data, such as one time passwords, etc., to the user devices 104, over the network 106. The users, such as customers and banking officials may interact through the user devices 104 with the authentication server 102. The authentication server 102 may be associated with a central repository (not shown in the FIG. 1), via the network 106, for storing sensitive data, pre-stored biometric data of the users, and the like. In one implementation, the central repository can be implemented as an internal repository within the authentication server 102.

According to the present subject matter, the authentication server 102 includes a visual signal generation module 108 configured to generate a visual flashing code based on encrypting the sensitive data to be transmitted to the user. The visual flashing code as described earlier is like a visual stimulus flickering/flashing at varied frequency levels.

Once generated, the visual signal generation module 108 transmits the visual flashing code to the user device 104, through the network 106. When the visual flashing code is received at the user device 104, a user viewing the visual flashing code plugs-in an EEG device and the biometric device(s) to the user device 104. The biometric device(s) obtains real-time biometric data of the user. For example, a fingerprint sensor obtains the fingerprints of the user. Further, the EEG device measures the brain activity of the user viewing the visual flashing code.

The real-time biometric data is received by the authentication server 102 based on which identity of the user is validated. To validate the identity, the authentication server 102 compares the real-time biometric data with the pre-stored biometric data of the user stored within the repository associated with the authentication server 102. If the comparison indicates a successful match, the user is authenticated. Subsequently, the authentication server 102 allows the user to decrypt the sensitive data contained in the visual flashing code.

In one implementation, the user device 104, includes, a visual signal decoding module 110 configured to decrypt the encrypted sensitive data contained in the visual flashing code. The visual signal decoding module 110, for example, receives brain signals contained in the EEG data, and interprets the brain signals based on a look-up table stored within the local memory of the user device 104. The brain signals may include frequency levels corresponding to which maximum amplitude are generated. The visual signal decoding module 110 receives such frequency levels and compares the same with the look-up table containing a list of frequency values corresponding to alphanumeric characters. An exemplary look up table is provided below.

TABLE 1

| Frequency in Hz | Action |
| --- | --- |
| 3 | X |
| 6 | x |
| 7 | 1 |

As shown in the table 1, the frequency level 3 Hz corresponds to alphabet "X", frequency level 6 Hz corresponds to alphabet "x", and frequency level 7 Hz corresponds to numeral "1", resulting in a decrypted sensitive data "Xx1". In one implementation, the visual signal decoding module 110 displays the decrypted sensitive data to the user.

Figure 2A:
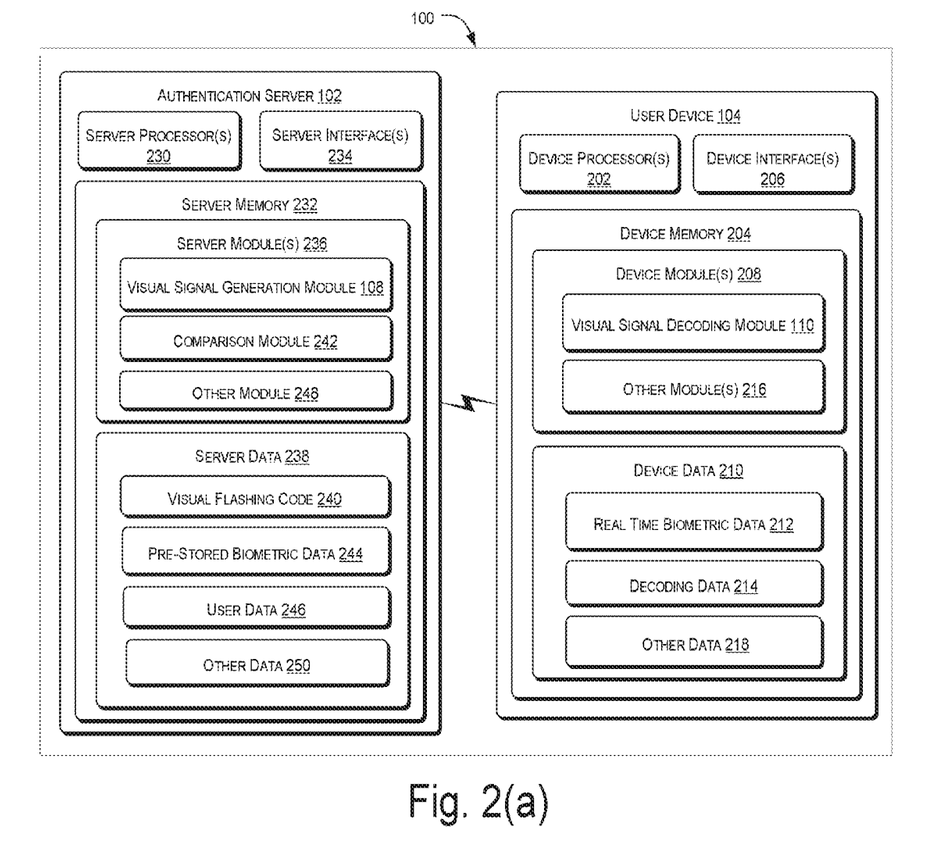
FIG. 2a illustrates components of the secure data communication system, according to an embodiment of the present subject matter.

FIG. 2(a) illustrates components of the secure data communication system 100, according to an embodiment of the present subject matter.

As shown in the figure, the secure data communication system 100 comprises an authentication server 102 connected to a user device 104 over a network, such as an internet. In said embodiment, the user device 104 includes one or more device processor(s) 202, a device memory 204 coupled to the device processor 202, and device interface(s) 206. The authentication server 102 includes one or more server processor(s) 230, a server memory 232 coupled to the server processor 230, and server interface(s) 234.

The device processor 202 and the server processor 230 can be a single processing unit or a number of units, all of which could include multiple computing units. The device processor 202 and the server processor 230 may be implemented as one or more microprocessors, microcomputers, microcontrollers, digital signal processors, central processing units, state machines, logic circuitries, and/or any devices that manipulate signals based on operational instructions. Among other capabilities, the device processor 202 and the server processor 230 are configured to fetch and execute computer-readable instructions and data stored in the device memory 204 and the server memory 232 respectively.

The device interfaces 206 and the server interfaces 234 may include a variety of software and hardware interfaces, for example, interface for peripheral device(s), such as a keyboard, a mouse, an external memory, a printer, etc. Further, the device interfaces 206 and the server interfaces 234 may enable the device 104 and the authentication server 102 to communicate with other computing devices, such as web servers and external databases. The device interfaces 206 and the server interfaces 234 may facilitate multiple communications within a wide variety of protocols and networks, such as a network, including wired networks, e.g., LAN, cable, etc., and wireless networks, e.g., WLAN, cellular, satellite, etc. The device interfaces 206 and the server interfaces 234 may include one or more ports to allow communication between the user device 104 and the authentication server 102.

The device memory 204 and the server memory 232 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The device memory 204 further includes device module(s) 208 and device data 210, and the server memory 232 further includes server module(s) 236 and server data 238.

The device modules 208 and the server modules 236 include routines, programs, objects, components, data structures, etc., which perform particular tasks or implement particular abstract data types. In one implementation, the device module(s) 208 include the visual signal decoding module 110 and device other module(s) 216. In said implementation, the server module(s) 236 include the visual signal generation module 108, a comparison module 242, and the server other module(s) 248. The device other module(s) 216 and the server other module(s) 248 may include programs or coded instructions that supplement applications and functions, for example, programs in the operating system of the user device 104 and the authentication server 102.

The device data 210 and the server data 238, amongst other things, serves as repositories for storing data processed, received, and generated by one or more of the device module(s) 208 and the server module(s) 236. The device data 210 includes real time biometric data 212, decoding data 214, and device other data 218. The server data 238 includes visual flashing code 240, pre-stored biometric data 244, user data 246, and server other data 250. The device other data 218 and the server other data 250 includes data generated as a result of the execution of one or more modules in the device other module(s) 216 and the server other modules 248.

According to the present subject matter, the authentication server 102 may be connected to the user device 104 as soon as a user access an application associated with the authentication server 102. Taking an example of an online banking, when a user access an online banking website through the user device 104, connectivity between the authentication server 102 and the user device 104 is established.

In one implementation, the authentication server 102 may perform an initial login-based authentication to authenticate the user. For example, a user may provide his login credentials in order to login to his personal banking profile. The login credentials may include, for example, a user identifier (ID) and a password. Based on the login credentials provided by the user, the authentication server 102 validate the identity of the user based on comparing the login credentials provided by the users with pre-stored login credentials. If the comparison indicates a match, the authentication server 102 allows a user to login to his personal banking profile.

Figure 2B:
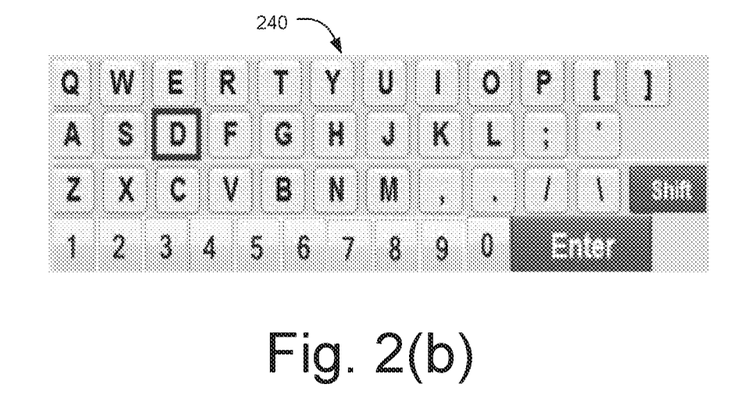
FIGS. 2(b)-2(d) illustrate examples of a visual flashing code, according to an embodiment of the present subject matter.
Figure 2C:
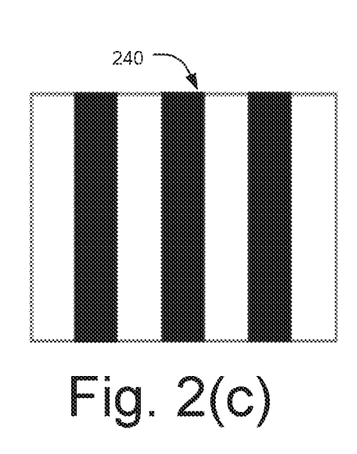
Figure 2D:
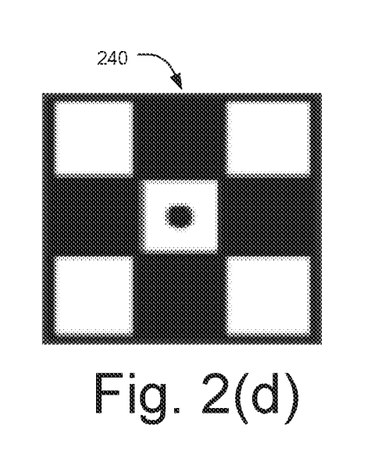

In order to carry out secure data exchange of sensitive data, for example, one time passwords, or other business transaction details, the visual signal generation module 108 of the authentication server 102 encrypts the sensitive data to generate a visual flashing code 240. The visual flashing code 240, thus, generated contains the encrypted sensitive data in the form of a visual stimulus. The visual signal generation module 108 may generate the visual flashing code 240 in various predefined patterns. The predefined patterns may include, but not limited to, a checkerboard pattern, black and white stripes pattern, or alpha-numeric keyboard pattern. FIGS. 2b-2d illustrates examples of the visual flashing code 240, according to an embodiment of the present subject matter. Specifically, FIG. 2b depicts an alpha-numeric keyboard pattern of the visual flashing code 240, FIG. 2c depicts black and white stripes pattern, and 2d depicts a checkerboard pattern of the visual flashing code 240.

Different patterns may flicker or flashes at varied frequency levels. In one implementation, a same pattern may flicker at different frequency levels. The visual signal generation module 108 transmits the visual flashing code 240 to a user device 104. In one implementation, a sequence of visual flashing codes 240 may be transmitted to the user device 104, depending upon the volume of the data to be transmitted.

The transmitted visual flashing code 240 is received at the user device 104, a user viewing the visual flashing code may connect the EEG device and the biometric device(s) to the user device 104. As described previously, real-time biometric data of the user is obtained by the biometric device. The biometric data may contain physical or behavioural traits of the user. For example, an ECG based biometric device measures heartbeat or an ECG profile of the user, and/or a fingerprint sensor captures fingerprints of the user On the other hand, the EEG device measures the brain activity of the user viewing the visual flashing code 240. As described previously, the visual flashing code 240 acts as a visual stimulus that flickers or flashes at varied frequency levels. In response to such a visual stimulus, a brain activity is recorded by the EEG device as the EEG data. The EEG device as described herein can be in the form a head band which can be connected to the user device 104, such as a desktop, mobile phone, etc either by a wired connection or a wireless connection.

The real-time biometric data obtained from the biometric device is received by a comparison module 242 of the authentication server 102 based on which the user is authenticated. For example, the comparison module 242 compares the real-time biometric data with the pre-stored biometric data 244 of the user stored within the repository associated with the authentication server 102. If the comparison results in a match, the user is authenticated, and comparison module 242 allows the user to decrypt the sensitive data contained in the visual flashing code 240. In one implementation, the comparison module 242 transmits authentication instructions to the user device 104. The authentication instructions may indicate whether the user is authenticated or not.

Based on the authentication or upon receiving the authentication instructions, a visual signal decoding module 110 of the user device 104 decrypt the sensitive data contained in the visual flashing code 240. For decryption, the visual signal decoding module 110 extract feature parameters from the EEG data. The extract feature parameters may be in form of an EEG graph depicting the relationship between the amplitude of the electrical signal and the frequency of the visual flashing code 240. The frequency of the visual flashing code 240 corresponding to which maximum amplitude is generated, is picked up, and compared with a look up table. The look up table as referred herein includes a list of frequency value corresponding to alphanumeric characters. Thus, based on the frequency levels, corresponding alphanumeric characters are picked up to decrypt the encrypted sensitive data. The visual signal decoding module 110 may display the decrypted data on the user device 104. In applications, such as online banking where the decrypted sensitive data is a password, the visual signal decoding module 110 may be configured to fill the decrypted data on the online banking website so that the user will be automatically logged-in to carry out the transactions.

Figure 3:
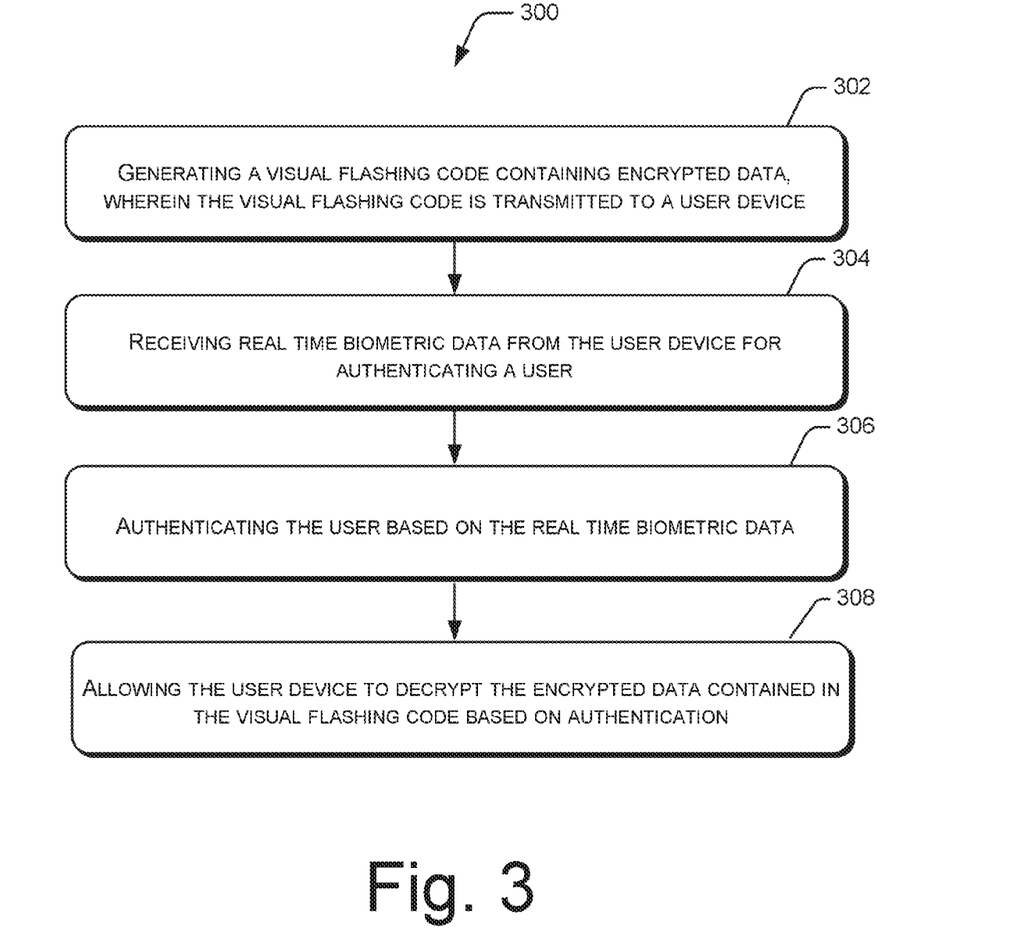
FIGS. 3-4 illustrate a method for secure data communication over a network, accordance to another embodiment of the present subject matter.
Figure 4:
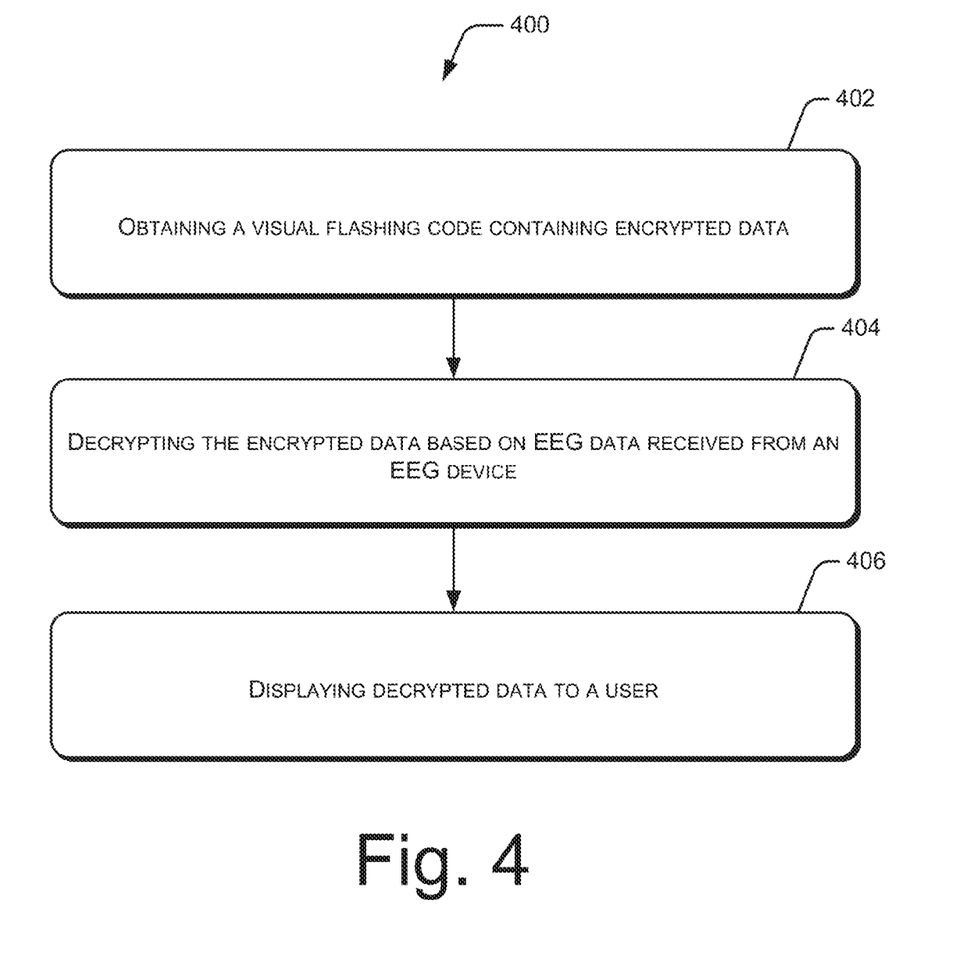

FIGS. 3-4 illustrate methods 300 and 400 for secure data communication, in accordance with an embodiment of the present subject matter. The methods 300 and 400 may be described in the general context of computer instructions can include routines, programs, objects, components, data structures, procedures, modules, functions, etc., that perform particular functions or implement particular abstract data types. The methods 300 and 400 may also be practiced in a distributed computing environment where functions or implement particular abstract data types. The methods 300 and 400 may also be practiced in a distributed computing environment where functions are performed by remote processing devices that are linked through a network. In a distributed computing environment, computer executable instructions may be located in both local and remote computer storage media, including memory storage devices.

The order in which the methods 300 and 400 are described is not intended to be construed as a limitation, and any number of the described method blocks can be combined in any order to implement the methods 300 and 400, or an alternative methods. Additionally, individual blocks may be deleted from the methods 300 and 400 without departing from the spirit and scope of the subject matter described herein. Furthermore, the methods 300 and 400 can be implemented in any suitable hardware, software, firmware, or combination thereof.

Referring to FIG. 3, the method 300 initiates at block 302, which involves generating a visual flashing code 240 containing encrypted data, wherein the visual flashing code 240 is transmitted to a user on a user device 104. The data referred herein may be sensitive data, such as a one time password, which is to be transmitted to the user. In one implementation, visual signal generation module 108 generates the visual flashing code 240 using a conventionally known visual code generation method.

At block 304, a real time biometric data of the user is received from the user device 104 with the help of biometric device(s), such as a fingerprint sensor, and/or an electrocardiogram (ECG) device connected to the user device 104 through a wired or a wireless connection. In one implementation, the comparison module 242 receives the real time biometric data 212.

At block 306, the user is authenticated based on the real time biometric data. For example, the real time biometric data is compared with a pre-stored biometric data 244. If the result of the comparison indicates a match, the user is authenticated. In one implementation, the comparison module 242 authenticates the user by comparing real time biometric data 212 received from the user device 104 with the pre-stored biometric data 244 in the authentication server 102.

At block 308, the user is allowed to decrypt the encrypted sensitive data contained in the visual flashing code based on the authentication. For example, if the user is authenticated, the comparison module 242 may transmit an authentication instructions indicating that a user is authenticated and thus allowed to decrypt the sensitive data.

Referring to FIG. 4, the method 400 initiates at block 402, where a visual flashing code 240 containing encrypted data is obtained from the user device 104. The visual signal decoding module 110, for example, receives the visual flashing code 240 containing the encrypted data. The data may include, for example, one time passwords (OTPs).

At block 404, the encrypted data contained in the visual flashing code 240 is decrypted based on EEG data received from an EEG device. The EEG data may contain brain signals indicative of brain activity of the user in response to viewing the visual flashing code 240. In one implementation, the visual signal decoding module 110 decrypts the encrypted data contained in the visual flashing code 240 based on the EEG data.

At block 406, the decrypted data is displayed to the user. The visual signal decoding module 110 may display the data to the user on the user device 104. In applications, such as online banking, e-commerce sites, where the data may be passwords or debit/credit card details, the decrypted data is not displayed to the user, rather the user can be automatically logged in subsequent to the decryption, thereby allowing the user to carry out the transactions.

Although embodiments for the secure data communication have been described in language specific to structural features and/or methods, it is to be understood that the invention is not necessarily limited to the specific features or methods described. Rather, the specific features and methods are disclosed as exemplary implementations for the secure data communication over the network.

We claim:

1. A method for secure data communication over a network, the method comprising:
   generating, from an authentication server, a visual flashing code containing encrypted data, wherein the visual flashing code is transmitted to a user on a user device;
   obtaining real time biometric data of the user from at least one biometric device connected to the user device;
   authenticating the user based on the real time biometric data; and
   allowing, based upon the user biometric authentication by the server, the user device to decrypt the encrypted data contained in the visual flashing code based on Electroencephalogram (EEG) data comprising brain signals indicative of brain activity of the user corresponding to the visual flashing code.

2. The method as claimed in claim 1, wherein the method further comprising:
   receiving login-credentials of the user from the user device; and
   comparing the login-credential of the user with pre-stored login credentials to validate identity of the user.

3. The method as claimed in claim 1, wherein the visual flashing code is generated in a predefined pattern.

4. The method as claimed in claim 3, wherein the predefined pattern is one of a checkerboard pattern, a black and white stripes pattern, and an alpha-numeric keyboard pattern.

5. The method as claimed in claim 1, wherein the authenticating comprises comparing the real time biometric data with pre-stored biometric data of the user.

6. A method for secure data communication over a network, the method comprising:
   obtaining, at a user device, a visual flashing code containing encrypted data from an authentication server; and
   decrypting, based on a real time biometric authentication of a user by the server, the encrypted data based on Electroencephalogram (EEG) data comprising brain signals indicative of brain activity of the user corresponding to the visual flashing code.

7. The method as claimed in claim 6, wherein the method further comprises displaying decrypted data on a user device.

8. The method as claimed in claim 6, wherein the method further comprises receiving the EEG data from an EEG device connected to a user device.

9. The method as claimed in claim 8, wherein the method further comprising comparing the EEG data with a look-up table to decrypt the encrypted data.

10. A user device for secure data communication over a network, wherein the user device comprising:
    a device processor; and
    a device memory coupled to the device processor, the device memory comprising:
    a visual signal decoding module configured to:
    obtain a visual flashing code from an authentication server, wherein the visual flashing code comprises encrypted data; and
    decrypt, upon a real time biometric authentication of a user by the server, an encrypted data based on electroencephalogram (EEG) data of the user corresponding to the visual flashing code, wherein the EEG data, comprising brain signals indicative of brain activity of the user corresponding to the visual flashing code, is obtained from an EEG device connected to the user device.

11. The user device as claimed in claim 10, wherein the EEG data comprises brain signals indicative of brain activity of the user in response to viewing the visual flashing code.

12. An authentication server comprising:
    a server processor; and
    a server memory coupled to the server processor, the server memory comprising:
    a visual signal generation module configured to generate a visual flashing code containing encrypting data to be transmitted to a user over a network; and
    a comparison module configured to:
    obtain real time biometric data of the user from at least one biometric device connected to a user device;
    compare the real time biometric data with a pre-stored biometric data of the user to authenticate the user; and
    allow, based upon the user biometric authentication, the user device to decrypt encrypted data contained in the visual flashing code based on electroencephalogram (EEG) data comprising brain signals indicative of brain activity of the user corresponding to the visual flashing code.

13. The authentication server as claimed in claim 12, wherein the at least one biometric device is any one of a fingerprint sensor, and an Electrocardiogram (ECG) device.

14. A non-transitory computer-readable medium having embodied thereon a computer program for executing a method comprising:
    obtaining, at a user device, a visual flashing code containing encrypted data from an authentication server; and
    decrypting, based on a real time biometric authentication of a user by the server, the encrypted data based on Electroencephalogram (EEG) data comprising brain signals indicative of brain activity of the user corresponding to the visual flashing code.

15. The computer-readable medium as claimed in claim 14, wherein the method further comprises displaying decrypted data on a user device.

16. The computer-readable medium as claimed in claim 14, wherein the method further comprising comparing the EEG data with a look-up table to decrypt the encrypted data.

17. A non-transitory computer-readable medium having embodied thereon a computer program for executing a method comprising:
    generating a visual flashing code containing encrypted data, wherein the visual flashing code is transmitted to a user on a user device from an authentication server;
    obtaining real time biometric data of the user from at least one biometric device connected to the user device;
    authenticating the user based on the real time biometric data; and
    allowing, based upon the user biometric authentication by the server, the user device to decrypt the encrypted data contained m the visual flashing code based on Electroencephalogram (EEG) data comprising brain signals indicative of brain activity of the user corresponding to the visual flashing code.

18. The computer-readable medium as claimed in claim 17, wherein the method further comprising:
    receiving login-credentials of the user from the user device; and
    comparing the login-credential of the user with pre-stored login credentials to validate identity of the user.

19. The computer-readable medium as claimed in claim 17, wherein the visual flashing code is generated in a predefined pattern, the predefined pattern being one of a checkerboard pattern, a black and white stripes pattern, and an alpha-numeric keyboard pattern.

20. The method as claimed in claim 17, wherein the authenticating comprises comparing the real time biometric data with pre-stored biometric data of the user.

* * * * *